United States Patent [19]

Nair et al.

[11] 4,221,907

[45] Sep. 9, 1980

[54] SUBSTITUTED O-α-D AND O-β-D-MULTI-GALACTOPYRANOSYL AND GLUCOPYRANOSYL 1→4 AND 1→6 GALACTOPYRANOSYL 1→6 α-D-GLUCOPYRANOSES

[75] Inventors: Vijay G. Nair, New York, N.Y.; Joseph P. Joseph, Montvale, N.J.; Seymour Bernstein, New City, N.Y.

[73] Assignee: American Cyanamid Company, Stamford, Conn.

[21] Appl. No.: 55,851

[22] Filed: Jul. 9, 1979

[51] Int. Cl.² .................... C07H 11/00; C07H 13/12; A61K 31/70
[52] U.S. Cl. ........................................ 536/118; 536/1; 424/180
[58] Field of Search .......................... 536/1, 118, 119; 424/180

[56] References Cited

U.S. PATENT DOCUMENTS

| | | |
|---|---|---|
| 4,021,544 | 5/1977 | Nair et al. .............................. 536/118 |
| 4,021,545 | 5/1977 | Nair et al. .............................. 536/118 |
| 4,066,829 | 1/1978 | Nair et al. .............................. 536/118 |

*Primary Examiner*—Johnnie R. Brown
*Assistant Examiner*—Blondel Hazel
*Attorney, Agent, or Firm*—Claude J. Caroli

[57] ABSTRACT

O-α-D (and O-β-D) multi-galactopyranosyl (and glucopyranosyl) 1→4 (and 1→6) galactopyranosyl 1→6-α-D-glucopyranose sulfate salts which are useful as complement inhibitors.

15 Claims, No Drawings

SUBSTITUTED O-α-D AND O-β-D-MULTI-GALACTOPYRANOSYL AND GLUCOPYRANOSYL 1→4 AND 1→6 GALACTOPYRANOSYL 1→6 α-D-GLUCOPYRANOSES

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (1968); The Johns Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–66; J. Allergy Clin. Immunol., 53, 298–302 (1974); Cold Spring Harbor Conf. Cell Proliferation 2/Proteases Biol. Control/229–241 (1975); Ann. Review of Biochemistry, 44, 697 (1975); Complement in Clinical Medicine, Disease-a-Month, (1975); Complement, *Scope*, December 1975; Annals of Internal Medicine, 84, 580–593 (1976); "Complement: Mechanisms and Functions", Prentice-Hall, Englewood Cliffs, N.J. (1976); Essays Med. Biochem., 2, 1–35 (1976); Hospital Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1–8, 1195, 1358–1364, 1482 (1977).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim. Biophys. Res. Comm., 67, 225–263 (1975); Ann. N.Y. Acad. Sci., 256, 441–450 (1975); Journal of Medicinal Chemistry, 19, 634–639, 1079 (1976); Journal of Immunology, 118, 466 (1977); Arch. Int. Pharmacodyn., 226, 281–285 (1977); Biochem. Pharmacol. 26, 325–329 (1977); Journal Pharm. Sci., 66, 1367–1377 (1977);

Chem. Pharm. Bull., 25, 1202–1208 (1977); Biochim. Biophys. Acta, 484, 417–422 (1977) and Journal Clin. Microbiology, 5, 278–284 (1977).

It has been reported that the known complement inhibitors epsilon-aminocaproic acid and tranexamic acid have been used with success in the treatment of hereditary angio-neurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Intern. Med., 84, 580–593 (1976); J. Allergy and Clin. Immunology, 60, 38–40 (1977).

It has also been reported that the drug pentosanpolysulfoester has an anticomplementary activity on human serum, both in vitro and in vivo, as judged by the reduction in total hemolytic complement activity; Pathologie Biologie, 25, 33–36, 25 (2), 105–108, 25 (3), 179–184 (1977).

SUMMARY OF THE INVENTION

This invention is concerned with compounds having complement inhibiting activity of the general formula I:

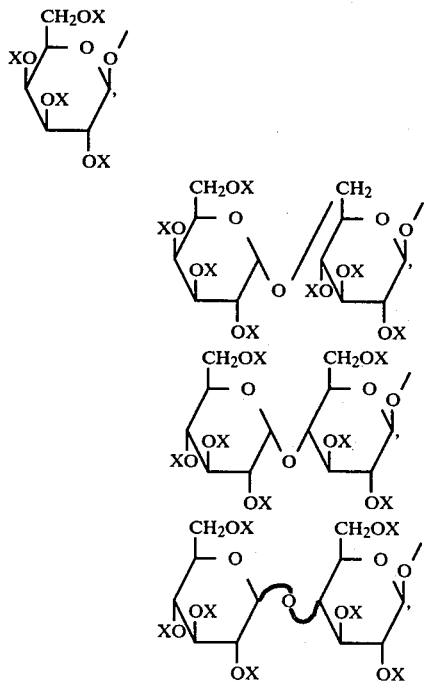

wherein X is SO$_3$A; wherein A is a pharmaceutically acceptable salt cation; and R is selected from the group consisting of OX,

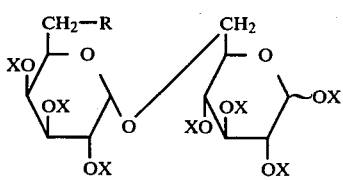

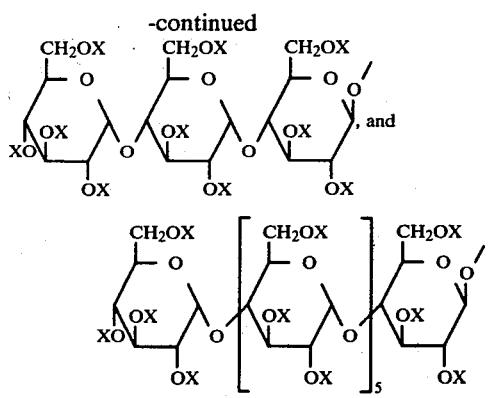

Specific compounds of the above formula I which are of interest as complement inhibitors are listed below. In this instance, these compounds are given both by their full name according to Chemical Abstracts nomenclature and then by an abbreviated nomenclature which is used throughout the balance of the specification and claims.

O-α-D-galactopyranosyl(1→6)-α-D-glucopyranose [gal 1α,6 glc] octakis (H-sulfate), octasalt with trimethylamine O-α-D-galactopyranosyl(1→6)-α-D-glucopyranose [gal 1α,6 glc] octakis (H-sulfate), octasodium salt O-β-D-galactopyranosyl(1→6)-O-α-D-galactopyranosyl(1→6)-α-D-glucopyranose [gal 1β,6 gal 1α,6 glc] undecakis (H-sulfate), undecasalt with trimethylamine O-β-D-galactopyranosyl(1→6)-O-α-D-galactopyranosyl(1→6)-α-D-glucopyranose [gal 1β,6 gal 1α,6 glc] undecakis (H-sulfate), undecasodium salt O-α-D-galactopyranosyl(1→6)-O-β-D-glucopyranosyl(1→6)-O-α-D-galactopyranosyl(1→6)-α-D-glucopyranose [gal 1α,6 glc 1β,6 gal 1α,6 glc] tetradecakis (H-sulfate), tetradecasalt with trimethylamine O-α-D-galactopyranosyl(1→6)-O-β-D-glucopyranosyl(1→6)-O-α-D-galactopyranosyl(1→6)-α-D-glucopyranose [gal 1α,6 glc 1β,6 gal 1α,6 glc] tetradecakis (H-sulfate), tetradecasodium salt O-α-D-glucopyranosyl(1→4)-O-β-D-glucopyranosyl(1→6)-O-α-D-galactopyranosyl(1→6)-D-glucopyranose [glc 1α,4 glc 1β,6 gal 1α,6 glc] tetradecakis (H-sulfate), tetradecasalt with trimethylamine O-α-D-glucopyranosyl(1→4)-O-β-D-glucopyranosyl(1→6)-O-α-D-galactopyranosyl(1→6)-D-glucopyranose [glc 1α,4 glc 1β,6 gal 1α,6 glc] tetradecakis (H-sulfate), tetradecasodium salt O-β-D-glucopyranosyl(1→4)-O-β-D-glucopyranosyl(1→6)-O-α-D-galactopyranosyl(1→6)-α-D-glucopyranose [glc 1β,4 glc 1β,6 gal 1α,6 glc] tetradecakis (H-sulfate), tetradecasalt with trimethylamine O-β-D-glucopyranosyl(1→4)-O-β-D-glucopyranosyl(1→6)-O-α-D-galactopyranosyl(1→6)-α-D-glucopyranose [glc 1β,4 glc 1β,6 gal 1α,6 glc] tetradecakis (H-sulfate), tetradecasodium salt O-α-D-glucopyranosyl(1→4)-O-α-D-glucopyranosyl(1→4)-O-β-D-glucopyranosyl(1→6)-O-α-D-galactopyranosyl(1→6)-α-D-glucopyranose [(glc 1α,4)₂ glc 1β,6 gal 1α,6 glc] heptadecakis(H-sulfate), heptadecasalt with trimethylamine O-α-D-glucopyranosyl(1→4)-O-α-D-glucopyranosyl(1→4)-O-β-D-glucopyranosyl(1→6)-O-α-D-galactopyranosyl(1→6)-α-D-glucopyranose [(glc 1α,4)₂ glc 1β,6 gal 1α,6 glc] heptadecakis(H-sulfate), heptadecasodium salt O-α-D-glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-O-α-D-galactopyranosyl(1→6)-D-glucopyranose [(glc 1α,4)₆ glc 1β,6 gal 1α,6 glc] nonacosakis (H-sulfate), nonacosasalt with trimethylamine O-α-D-glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-O-α-D-galactopyranosyl(1→6)-D-glucopyranose [(glc 1α,4)₆ glc 1β,6 gal 1α,6 glc] nonacosakis (H-sulfate), nonacosasodium salt This invention is also concerned with a method of inhibiting the complement system in a body fluid, such as blood serum, which comprises subjecting body fluid complement to the action of an effective complement inhibiting amount of a compound as described hereinabove. The method of use aspect of this invention is further concerned with a method of inhibiting the complement system in a warm-blooded animal which comprises administering to said animal an effective complement inhibiting amount of a compound as described hereinabove. Body fluid can include blood, plasma, serum, synovial fluid, cerebrospinal fluid, or pathological accumulcations of fluid such as pleural effusion, etc.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The instant compounds may also be used in the therapeutic treatment of warm-blooded animals having non-immunologic diseases such as paroxysmal nocturnal hemoglobinurea, hereditary antioneurotic edema (treated with Suramin Sodium, etc.) and inflammatory states induced by the action of bacterial of lysosomal enzymes on the appropriate complement components as for example, inflammation following coronary occlusion. They may also be useful in the treatment of transplant rejection and as blood culture and transport mediums.

DESCRIPTION OF THE INVENTION

The compounds of the present invention may be prepared according to the following flowchart.

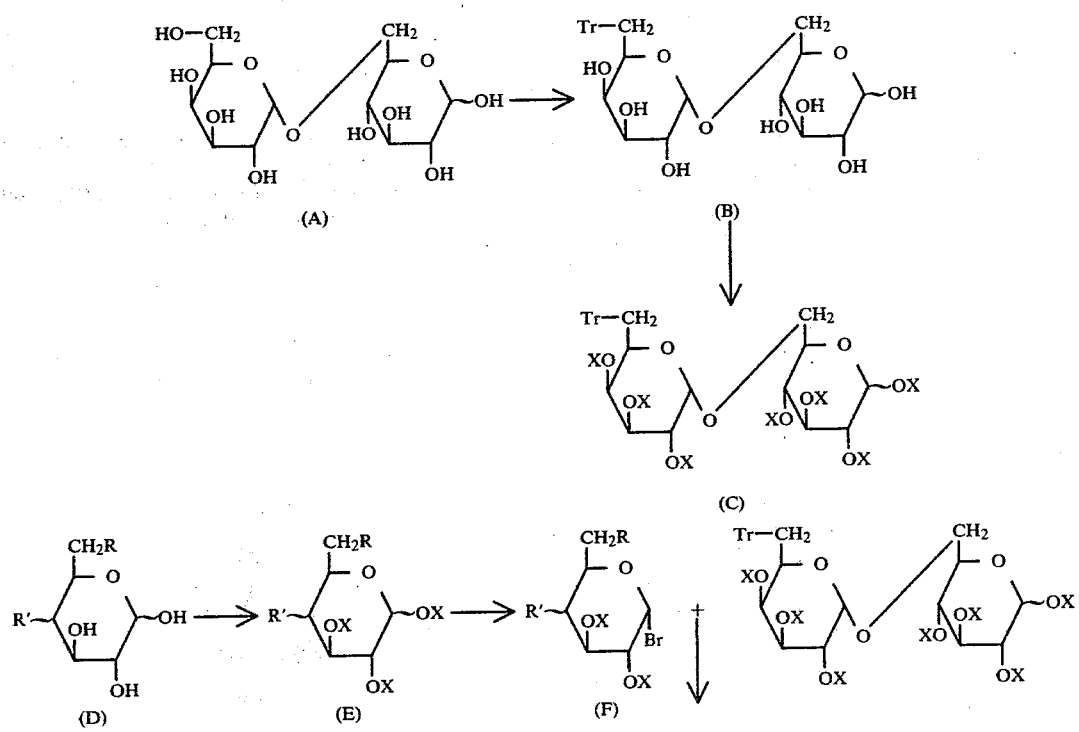

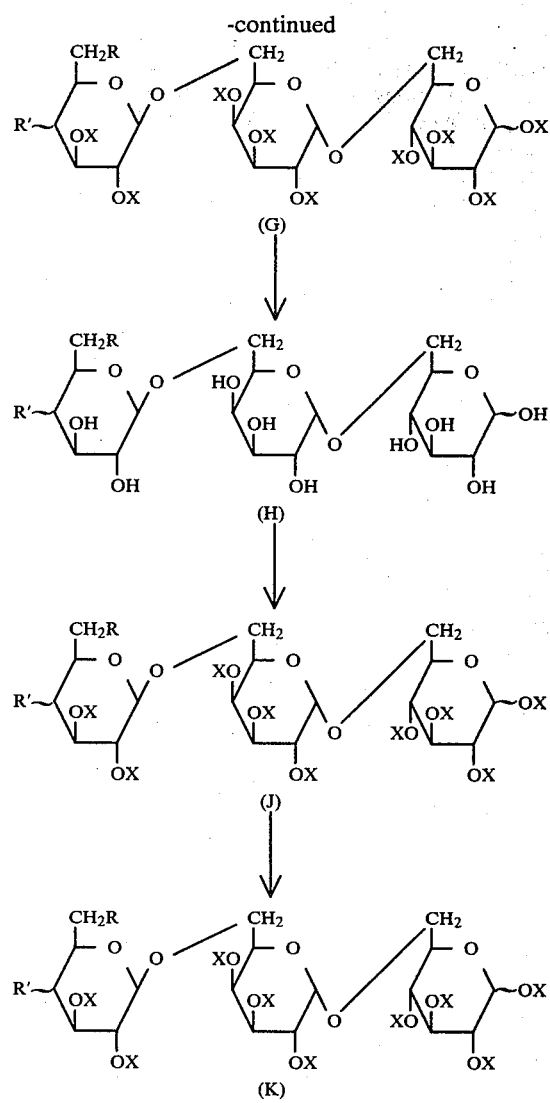

In accordance with the above flowchart gal $1\alpha,6$ glc (A) is dissolved in pyridine containing anhydrous calcium sulfate with warming. Trityl chloride is added and the mixture is heated producing trityl gal $1\alpha,6$ glc (B). Further treatment with acetic anhydride and extraction into methylene chloride produces trityl peracetyl gal $1\alpha,6$ glc (C).

The compound (D) where R and R' are selected from the following grouped pairs,

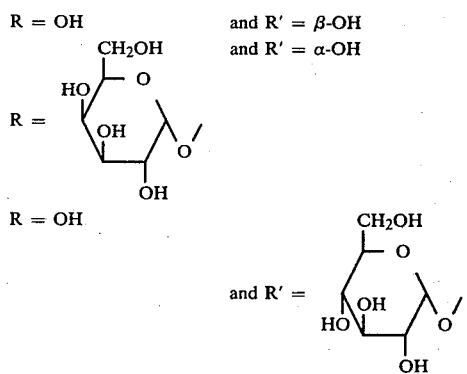

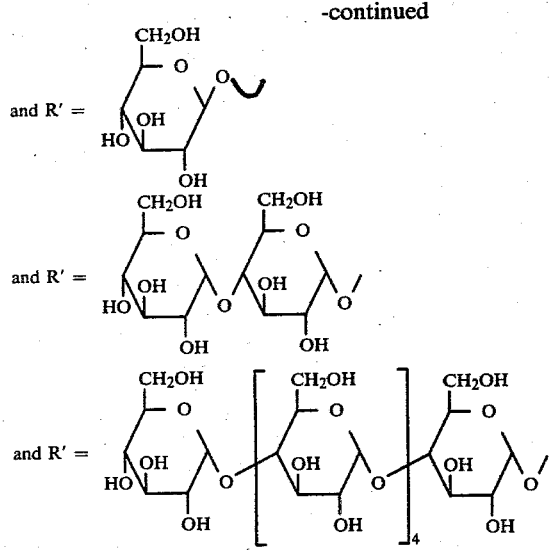

is converted to the corresponding compound (E) where X is COCH₃ by conventional methods. Compound (E) is then brominated using hydrobromic acid in glacial acetic acid and extracting in methylene chloride to give the bromo polyacetyl sugar (F).

Compound (F) and (C) are then reacted with silver trifluorosulfonate in nitromethane containing calcium sulfate under anhydrous conditions and at reduced temperature. The product is extracted in methylene chloride treated with acetic anhydride in pyridine and subjected to conventional purification by chromatography to give (G) where X is COCH₃.

The polyacetates (G) are then reduced to the sugars (H) by reaction in a 6:2:3 mixture of methanol, water and triethylamine for a period of several hours. The product (H) is extracted from methanol and ether.

The sugars (H) are converted to the poly (H-sulfate) poly salts with trimethylamine (J) where X is SO₃H.N(CH₃)₃, by treatment with trimethylamine sulfur trioxide in dimethylformamide with heat for several hours. The product (J) is extracted from ethanol.

The product (J) is converted to the poly (H-sulfate) poly alkali metal salt (K) by treatment with an alkali metal acetate or alkali hydroxide in trimethylamine. The product (K) is precipitated by ethanol.

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent uon the function of complement, such as inflammatory process and cell membrane damage induced by antigen-antibody complexes. The range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dose for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanolamine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable for unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of the simultaneous controls; (vi) Complement Level Reduction Test—In this test, the above dosed guinea pigs, or others are bled for serum and the complmenet level is determined in undiluted serum by the capillary tube method of U.S. Pat. No. 3,876,376 and compared to undosed control guinea pigs; (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with resulrs of tests code 026,035, 036, Cap 50, % inhibition. Table I shows that the compounds of the invention possess highly significant in vitro and in vivo complement inhibiting activity in warm-blooded animals. Results obtained are listed in Table I.

Table I

| | Biological Activities | | | | In vivo Activity (Guinea Pig) % Inhibition Intraperitoneal Time (Min.) | | |
|---|---|---|---|---|---|---|---|
| Compound | C1 026* Wells | C-Late 035* Wells | Shunt Inhibition 036* Wells | Cap 50 | 30 | 60 | 120 |
| gal 1α,6 → glc octakis (H-sulfate), octasodium salt | +8** | N | N | 407 | | | |
| gal 1β,6 → gal 1α,6 → glc undecakis (H-sulfate), undecasalt with trimethylamine | +9 | N | N | 279 | | | |
| gal 1β,6 → gal 1α,6 → glc undecakis (H-sulfate), undecasodium salt | +9 | N | N | <100 | −30 | −17 | −56 (5/5) |

Table I-continued

| | Biological Activities | | | | In vivo Activity (Guinea Pig) % Inhibition Intraperitoneal Time (Min.) | | |
|---|---|---|---|---|---|---|---|
| Compound | Cl 026* Wells | C-Late 035* Wells | Shunt Inhibition 036* Wells | Cap 50 | 30 | 60 | 120 |
| gal 1α,6 → glc 1β,6 → gal 1α,6 → glc tetradecakis (H-sulfate), tetradecasalt with trimethylamine | +9 | +1 | +5 | 110 | | | |
| gal 1α,6 → glc 1β,6 → gal 1α,6 → glc tetradecakis (H-sulfate), tetradecasodium salt | +9 | +1 | +6 | 93 | −44 | −55 | −80 |
| glc 1α,4 → glc 1β,6 → gal 1α,6 → glc tetradecakis (H-sulfate), tetradecasalt with trimethylamine | +9 | +1 | +5 | 187 | | | |
| glc 1α,4 → glc 1β,6 → gal 1α,6 → glc tetradecakis (H-sulfate), tetradecasodium salt | +10 | +1 | +6 | 112 | −54 | −45 | −39 |
| glc 1β,4 → glc 1β,6 → gal 1α,6 → glc tetradecakis (H-sulfate), tetradecasalt with trimethylamine | +9 | N | +4 | 247 | | | |
| glc 1β,4 → glc 1β,6 → gal 1α,6 → glc tetradecakis (H-sulfate), tetradecasodium salt | +9 | N | N | 86 | −25 | −34 | −60 |
| (glc 1α,4) → glc 1β,6 → gal 1α,6 → glc heptadecakis (H-sulfate)$^2$, heptadecasalt with trimethylamine | +9 | +1 | N | 152 | | | |
| (glc 1α,4) → glc 1β,6 → gal 1α,6 → glc heptadecakis (H-sulfate)$^2$, heptadecasodium salt | +9 | +2 | +6 | 116 | | | |
| (glc 1α,4) → glc 1β,6 → gal 1α,6 → glc nonacosakis (H-sulfate)$^6$, nonacosasalt with trimethylamine | +10 | +1 | +5 | 420 | | | |
| (glc 1α,4) → glc 1β,6 → gal 1α,6 → glc nonacosakis (H-sulfate)$^6$, nonacosasodium salt | +9 | +3 | +5 | 193 | | | |

*Tests identified by code herein
**Activity in wells, a serial dilution assay; higher well number indicates higher activity. The serial dilutions are two-fold

DETAILED DESCRIPTION OF THE INVENTION

The following examples describe in detail the preparation and formulation of representative compounds of the present invention.

EXAMPLE 1

Gal 1α,6 glc octakis (H-sulfate), octasalt with trimethylamine

A 1.44 g. portion of gal 1α,6 glc and 5.5 g. of trimethylamine sulfur trioxide are added to 75 ml. of dimethylformamide and heated at 65°–70° C. for 20 hours. The crystals are recovered, triturated repeatedly with dimethylformamide and then with acetone, then filtered, washed with ether and dried, giving the desired product as a colorless granular solid.

EXAMPLE 2

Gal 1α,6 glc octakis (H-sulfate), octasodium salt

A 3.0 g. portion of gal 1α,6 glc octakis (H-sulfate), octasalt with trimethylamine is dissolved in 10 ml. of water. A 10 ml. portion of 30% aqueous sodium acetate solution is added and the mixture is filtered. The filtrate is allowed to stand for about 10 minutes and then absolute ethanol is added, producing a gum. The gum is collected and triturated with absolute ethanol producing a granular solid. This solid is washed four times with absolute ethanol and twice with anhydrous ether. The solid is redissolved in 10 ml. of water, 10 ml. of 30% sodium acetate solution is added and the process is repeated, giving the desired product as a colorless granular solid.

EXAMPLE 3

Gal 1β,6 gal 1α,6 glc undecaacetate

A 51.3 g. portion of gal 1α,6 glc (dried at 78° C. for 20 hours over phosphorous pentoxide) and 25 g. of anhydrous calcium sulfate are added to 750 ml. of pyridine and the mixture is warmed. When partially dissolved at 60°–70° C., 46.1 g. of trityl chloride is added and the mixture is heated at 90° C. on a steam bath for 3 hours. The mixture is cooled to 45° C. and the liquid is recovered by decantation. To this liquid is added 150 ml. of acetic anhydride, the mixture is allowed to stand at room temperature for 18 hours and then poured into 2½ liters of ice and water with vigorous mechanical stirring. Stirring is continued for 2 hours and then the mixture is filtered. The gummy white solid is collected, washed with water, air dried and then dissolved in methylene chloride. This solution is dried over magnesium sulfate, filtered and evaporated to a gum. This gum is dissolved in about 400 ml. of methanol and poured into 3000 ml. of water with stirring. The white solid is collected and dried, giving 110.8 g. of trityl peracetyl gal 1α,6 glc.

A 3.84 g. portion of silver triflate is added to 100 ml. of nitromethane containing 10 g. of anhydrous calcium sulfate and stirred at room temperature for 5 minutes. The mixture is cooled in an ice bath and 8.8 g. of trityl peracetyl gal 1α,6 glc is added. The mixture is stirred and then 6.16 g. of acetobromogalactose is added with vigorous stirring at 0° C. for one hour. The mixture is warmed on a steam bath for 2 minutes, cooled, diluted with methylene chloride and filtered. The filtrate is washed with water and then saturated sodium bicarbonate solution and dried over anhydrous sodium sulfate. Evaporation of the solvent in vacuo gives a pale cream colored glassy solid. This solid is dissolved in 50 ml. of pyridine and 40 ml. of acetic anhydride is added. The mixture is stirred overnight at room temperature, poured into ice water and the resulting precipitate is collected and washed with water. This solid is dissolved in 250 ml. of methylene chloride and dried over anhydrous sodium sulfate. Evaporation of the solvent in vacuo gives a pale cream colored glass. This solid is passed through a silica gel chromatographic column using the system ethyl acetate:hexane (60:40). The first two fractions give the desired product.

EXAMPLE 4

Gal 1β,6 gal 1α,6 glc

A 2.4 g. portion of gal 1β,6 gal 1α,6 glc undecaacetate is dissolved in 55 ml. of a mixture of methanol, water and triethylamine [6:2:3]. The clear solution is stirred at room temperature for 22 hours and then evaporated to dryness in vacuo. The residue is dissolved in 50 ml. of water and treated with a small amount of Amberlite ® IR-120 (H+ form) and charcoal and then filtered through celite. The filtrate is evaporated to dryness in vacuo giving the desired product as a colorless glass.

EXAMPLE 5

Gal 1β,6 gal 1α,6 glc undecakis (H-sulfate), undecasalt with trimethylamine

A 4.95 g. portion of trimethylamine sulfur trioxide is dissolved in 25 ml. of dimethylformamide by warming to 70° C. A 1.1 g. portion of gal 1β,6 gal 1α,6 glc is added and the solution is stirred at 70° C. for 20 hours. The mixture is cooled to room temperature. The gum is collected and triturated with absolute ethanol giving a granular solid which is collected, washed with absolute ethanol and then anhydrous ether and dried in vacuo giving the desired product as a colorless product.

EXAMPLE 6

Gal 1β,6 gal 1α,6 glc undecakis (H-sulfate), undecasodium salt

A 1.8 g. portion of gal 1β,6 gal 1α,6 glc undecakis (H-sulfate), undecasalt with trimethylamine is dissolved in 5 ml. of water. A 10 ml. portion of 30% aqueous sodium acetate solution is added and the mixture is swirled and allowed to stand for 15-20 minutes. A 75 ml. portion of absolute ethanol is added and the mixture is stirred vigorously. The resulting gum is collected and triturated repeatedly with absolute ethanol. The resulting granular solid is recovered, washed with absolute ethanol and then anhydrous ether and dried in vacuo, giving the desired product as an off-white granular solid.

EXAMPLE 7

Gal 1α,6 glc 1β,6 gal 1α,6 glc, tetradecaacetate

A 50 ml. portion of 30-32% hydrobromic acid in glacial acetic acid is cooled in an ice bath and a solution of 10.0 g. of gal 1α,6 glc octaacetate in 80 ml. of chloroform is added with shaking. The mixture is allowed to stand in the ice bath for 2 hours with occasional swirling and then poured into crushed ice with vigorous swirling. The mixture is extracted with 100 ml. of chloroform and the aqueous layer is washed twice with 75 l. portions of chloroform. The chloroform extracts are combined and washed with ice-cold water until neutral. The organic layer is dried over anhydrous calcium chloride and evaporated to dryness in vacuo giving gal 1α,6 glc heptaacetyl bromide as a pale yellow glass.

A 5.0 g. portion of anhydrous calcium sulfate and 995 mg. of silver perchlorate are added to 50 ml. of nitromethane and the mixture is cooled in an ice bath for 10 minutes. A 3.52 g. portion of trityl peracetyl gal 1α,6 glc is added with stirring followed by the rapid addition of 3.36 g. of gal 1α,6 glc heptaacetyl bromide with vigorous stirring. for 10 minutes. The mixture is warmed on a steam bath for 5 minutes, cooled to room temperature, diluted with 150 ml. of methylene chloride and filtered. The filtrate is washed with water and then with saturated aqueous sodium bicarbonate solution. The organic extract is dried over anhydrous sodium sulfate and evaporated in vacuo to a yellow paste. This paste is dissolved in 20 ml. of a 1:1 mixture of pyridine and acetic anhydride and stirred at room temperature overnight. It is then poured dropwise with stirring into ice-water. The resulting gum is recovered, dissolved in a small volume of ethanol, and poured dropwise with stirring into ice-water. The resulting brown solid is collected, washed with cold water and air dried. This solid is dissolved in small volume of methylene chloride and appllied to a 100 g. silica gel column prepared in hexane. Elution is started with hexane and then gradually changed to hexane containing ethyl acetate. The product is eluted in the fractions of 25-40% ethylacetate in hexane which are pooled and evaporated to dryness in vacuo. This product is further purified by chromatography on thick silica layer plates, eluting with ethyl acetate:hexane (60:40). The band with the desired product is removed from the plates and extracted into ethyl acetate. The silica is removed by filtration and the ethyl acetate extract is evaporated to dryness in vacuo giving the desired product.

EXAMPLE 8

Gal 1α,6 glc 1β,6 gal 1α,6 glc

A 2.0 g. portion of gal 1α,6 ,6 glc 1β,6 gal 1α,6 glc tetradecaacetate is dissolved in 55 ml. of a mixture of methanol anol, water and triethylamine (6:2:3) and reacted as described in Example 4, giving the desired product as a colorless glass.

EXAMPLE 9

Gal 1α,6 gls 1β,6 gal 1α,6 glc tetradecakis (H-sulfate), tetradecasalt with trimethylamine A 4.5 g portion of trimethylamine sulfur trioxide is dissolved in 25 ml. of dimethylformamide with stirring at 70° C. A 1.0 g. portion of gal 1α,6 glc 1β,6 gal 1α,6 glc is added and the reaction proceeds as described in Example 5, giving the desired product as a pale brown granular solid.

EXAMPLE 10

Gal 1α,6 glc 1β,6 gal 1α,6 glc tetradecakis (H-sulfate), tetradecasodium salt

A 3.4 g. portion of gal 1α,6 glc 1β, 6 gal 1α, 6 glc tetradecakis (H-sulfate), tetradecasalt with trimethylamine is dissolved in 10 ml. of water. A 10 ml. portion of 30% aqueous sodium acetate solution is added and the reaction proceeds as described in Example 6, giving the desired product as a pale brown granular solid.

EXAMPLE 11

Glc 1α,4 → glc 1β, 6 → gal 1α, 6 → glc tetradecaacetate

A suspension of 50 g. of anhydrous sodium acetate in 500 ml. of acetic anhydride is heated to boiling and 100 g. of glc 1α, 4 → glc monohydrate is added slowly and portionwise to maintain boiling. The mixture is boiled vigorously, cooled to about 150° C. and poured into 2 liters of vigorously stirred ice and water. The mixture of gum and solid is separated by decantation and fresh ice and water are added. After standing for 4 hours the solid is collected, dissolved in 500 ml. of methylene chloride, washed once with water, once with saturated sodium bicarbonate solution, twice with water, dried over sodium sulfate, filtered through diatomaceeous earth, washed with methylene chloride and evaporated to a gum. This gum is recrystallized several times from ethanol, giving glc 1α,4 → glc octaacetate as a white solid.

A 1.5 g. portion of glc 1α,4 → glc octaacetate is added to 7.5 ml. of 30–32% hydrobromic acid in glacial acetic acid cooled to 0°–5° C. in an ice bath. The solution is stored at 0°–5° C. for 2½ hours, then 30 ml. of methylene chloride are added. The mixture is washed with ice water until neutral to Congo Red paper, dried over sodium sulfate, filtered and evaporated to a solid which is glc 1α,4 → glc heptaacetyl bromide.

A 622 mg. portion of silver perchlorate is dissolved in 10 ml. of nitromethane with warming. A 250 mg. portion of anhydrous calcium sulfate is added and the mixture is cooled to 0°–5° C. An 880 mg. portion of trityl peracetyl gal 1α,6 → glc is added, followed by 860 mg. of glc 1α,4 → glc heptaacetyl bromide. The mixture is warmed slightly to complete the reaction then filtered and washed with nitromethane. The combined filtrate and washings is washed with cold saturated sodium bicarbonate solution, then twice with cold water, dried over sodium sulfate, filtered and evaporated to a gum. Ether is added to the gum and the mixture is evaporated giving a yellow glass. This glass is dissolved in 10 ml. of pyridine and 5 ml. of acetic anhydride is added. After standing at room temperature for 18 hours the mixture is poured into ice-water giving a white solid which is collected, washed several times with water and air dried. Chromatography of this solid as described in Example 7 gives a band containing the product which is eluted with acetone, filtered and evaporated to a glass. This glas is dissolved in ether, filtered and then evaporated giving the desired product as a colorless glass.

EXAMPLE 12

Glc 1α,4 → glc 1β,6 → gal 1α,6 → glc

A 1.0 g. portion of glc 1α,4 → glc 1β,6 → gal 1α,6 → glc tetradecaacetate is dissolved in a solution of 2 parts methanol, one part water and one part triethylamine. The procedure of Example 4 is followed, giving the desired product as a glass.

EXAMPLE 13

Glc 1α,4 → glc 1β,6 → gal 1α,6 → glc tetradecakis (H-sulfate), tetradecasalt with trimethylamine A 200 mg. portion iof glc 1α,4 → glc 1β, 6 → gal 1α,6 → glc is dissolved in 5 ml. of dimethylformamide and 1.4 g. of trimethylamine sulfur trioxide is added. The procedure of Example 5 is followed giving the desired product as a glass.

EXAMPLE 14

Glc 1α,4 → glc 1β,6 → gal 1α,6 → glc tetradecakis (H-sulfate), tetradecasodium salt A 500 mg. portion of glc 1α,4 → glc 1β,6 → gal 1α,6 → glc tetradecakis (H-sulfate), tetradecasodium salt with trimethylamine is added to 4 ml. of water and the mixture is filtered. To the filtrate is added 2 ml. of 30% aqueous sodium acetate solution and the procedure of Example 6 is followed, giving the desired product as a white solid.

EXAMPLE 15

Glc 1β,4 → glc 1β,6 → gal 1β,6 → glc tetradecaacetate

Glc 1β,4 → glc is converted to its octaacetate form by conventional methods as disclosed in Methods of Carbohydrate Chemistry 1, 334. A 20 g. portion of this octaacetate is dissolved in 200 ml. of methylene chloride and the solution is cooled to 0° C. An 80 ml. portion of 32% hydrobromic acid in glacial acetic acid is added and the mixture is allowed to stand in an ice bath for 2 hours. The mixture is then poured into crushed ice and diluted with 200 ml. of methylene chloride. The organic layer is separated, washed repeatedly with ice water until neutral, dried over anhydrous sodium sulfate and evaporated in vacuo, giving glc 1β,4 → glc heptaacetate bromide as a white solid.

A 1.92 g. portion of silver tritylate and 10 g. of anhydrous calcium sulfate are added to 100 ml. of nitromethane. The mixture is stirred for 5 minutes, then cooled in an ice bath and 4.4 g. of trityl peracetyl gal 1α,6 → glc is added. A 5.25 g. portion of glc 1β,4 → glc heptaacetate bromide is added with vigorous stirring and the mixture is stirred in an ice bath for one hour. The mixture is diluted with 125 ml. of methylene chloride and filtered through diatomaceous earth. The filtrate is washed with water and then with saturated aqueous sodium bicarbonate solution. The organic layer is separated, dried over anhydrous sodium sulfate and evaporated in vacuo to a light brown glass.

This glass is dissolved in 50 ml. of pyridine and 30 ml. of acetic anhydride is added. The mixture is stirred at room temperature for 20 hours and then poured in a thin stream into ice water with vigorous stirring. The precipitate which forms is collected, washed with cold water and dried. This solid is subjected to chromatography on silica gel plates using ethyl acetate:hexane (60:40) giving the desired product.

EXAMPLE 16

Glc 1β,4 → glc 1β,6 → gal 1α,6 → glc

A 1.6 g. portion of glc 1β,4 → glc 1β,6 → gal 1α,6 → glc tetradecaacetate is dissolved in 22 ml. of a mixture of triethylamine, water and methanol (3:2:6). The mixture is treated as described in Example 4, giving the desired product as an off-white glass.

EXAMPLE 17

Glc 1β,4 → glc 1β,6 → gal 1α,6 → glc tetradecakis (H-sulfate), tetradecasalt with trimethylamine A 4.1 g. portion of trimethylamine sulfur trioxide is dissolved in 15 ml. of dimethylformamide by warming to 70° C. An 800 mg. portion of glc 1β,4 → glc 1β,6 → gal 1α,6 → glc is added and the procedure of Example 5 is

EXAMPLE 18

Glc 1β,4 glc 1β,6 gal 1α,6 glc tetradecakis (H-sulfate), tetradecasodium salt

A 2.0 g. portion of glc 1β,4 glc 1β,6 gal 1α,6 glc tetradecakis (H-sulfate), tetradecasalt with trimethylamine is dissolved in 10 ml. of water. A 10 ml. portion of 30% aqueous sodium acetate solution is added and the reaction proceeds as described in Example 6, giving the desired product as a light brown powder.

EXAMPLE 19

(Glc 1α,4)2glc 1β,6 gal 1α,6 glc heptadecaacetate

A mixture of 5 g. of anhydrous sodium acetate and 50 ml. of acetic anhydride is heated to vigorous boiling. A 10 g. portion of glc 1α,4 glc 1α,4 glc is added in small portions. The mixture is boiled vigorously for a few minutes, cooled to 50°-60° C. and then poured in a thin stream into crushed ice with vigorous stirring. The oil which separates is redissolved in ethanol and then poured over crushed ice. The colorless precipitate which forms is collected, washed with ice-cold water, dried and crystallized from ethanol-water giving glc 1α,4 glc 1α,4 glc hendecaacetate as colorless crystals.

A 75 ml. portion of 30-32% hydrobromic acid in glacial acetic acid is cooled in an ice bath. A solution of 15.0 g. of glc 1α,4 glc 1α,4 glc hendecaacetate in 125 ml. of chloroform is added with swirling and the mixture is allowed to stand in the ice bath for 2 hours with occasional swirling. The mixture is poured onto crushed ice and diluted with 200 ml. of methylene chloride. The organic layer is washed with ice-cold water until neutral, dried over anhydrous calcium chloride and evaporated in vacuo to a colorless glass, which is glc 1α,4 glc 1α,4 glc decaacetate bromide.

A 995 mg. portion of silver perchlorate and 5.0 g. of anhydrous calcium sulfate are added to 50 ml. of nitromethane. The mixture is stirred for 5 minutes, then cooled in an ice bath and 3.52 g. of trityl peracetyl gal 1α,6 glc is added. A 3.91 g. portion of glc 1α,4 glc 1α,4 glc decaacetate bromide is added with vigorous stirring and the mixture is stirred in an ice bath for 10 minutes, then warmed on a steam bath for 5 minutes, cooled to room temperature, diluted with 150 ml. of methylene chloride and filtered. The filtrate is washed with water and then with saturated aqueous sodium bicarbonate solution. The organic extract is separated, dried over anhydrous sodium sulfate and evaporated in vacuo to a pale yellow glass. This glass is dissolved in 25 ml. of pyridine and 10 ml. of acetic anhydride is added. The mixture is allowed to stand at room temperature overnight and then poured into crushed ice. The precipitate is collected, washed with water, dried and chromatographed on a silica gel column, eluting with ethyl acetate:hexane (1:1) giving the desired product.

EXAMPLE 20

(Glc 1α,4)2 glc 1β,6 gal 1α,6 glc

A solution of 1.8 g. of glc 1α,4 glc 1α,4 glc 1β,6 gal 1α,6 glc heptadecaacetate in 55 ml. of a mixture of methanol, water and triethylamine (6:2:3) is reacted as described in Example 4, to give the desired product as a colorless glass.

EXAMPLE 21

(Glc 1α,4)2 glc 1β,6 gal 1α,6 glc heptadecakis (H-sulfate) heptadecasalt with trimethylamine A 3.5 g. portion of trimethylamine sulfur trioxide is dissolved in 25 ml. of dimethylformamide with warming to 70° C. An 828 mg. portion of glc 1α,4 glc 1α,4 glc 1β,6 gal 1α,6 glc is added and the procedure of Example 5 is followed, giving the desired product as a pale brown granular solid.

EXAMPLE 22

(Glc 1α,4)2 glc 1β,6 gal 1α,6 glc heptadecakis (H-sulfate) heptadecasodium salt

A reaction mixture comprising 2.45 g. of glc 1α,4 glc 1α,4 glc 1β,6 gal 1α,6 glc tetradecakis (H-sulfate) heptadecasalt with trimethylamine, 10 ml. of water and 10 ml. of 30% aqueous sodium acetate solution is treated as described in Example 6, giving the desired product as a pale brown granular solid.

EXAMPLE 23

(Glc 1α,4)6 glc 1β,6 gal 1α,6 glc nonacosaacetate (Glc 1α,4)6 glc is converted to its polyacetate form by conventional methods as described in Methods in Carbohydrate Chemistry 1, 334. A 10 g. portion of this polyacetate is dissolved with warming in 15 ml. of glacial acetic acid. To this is added 100 ml. of cold (0°-5° C.) 32% hydrobromic acid in glacial acetic acid. The mixture is stirred for 2½ hours in an ice bath, then diluted with 100 ml. of methylene chloride and washed with ice-water until neutral to Congo Red paper. The solution is dried over magnesium sulfate, filtered and evaporated to a white glass which is (glc 1α,4)6 glc polyacetate bromide.

A 2.72 g. portion of trityl peracetyl gal 1α,6 glc which has been previously dried, is dissolved in 50 ml. of dry nitromethane. A 3 g. portion of anhydrous calcium sulfate and 1.2 g. of silver trifluorosulfonate are added. The mixture is cooled with stirring in an ice bath and 10 g. of (glc 1α,4)6 glc polyacetate bromide in 50 ml. of dry nitromethane is added. The mixture is stirred at 0°-5° C. for one hour, filtered and the filter cake is washed with nitromethane. The filtrate is diluted with 100 ml. of methylene chloride, washed with cold saturated aqueous sodium bicarbonate solution, then twice with water, dried over magnesium sulfate, filtered and evaporated to a glass. This glass is dissolved in 10 ml. of pyridine and 3 ml of acetic anhydride is added. The mixture is allowed to stand 48 hours at room temperature, then poured into ice water giving a tam solid which is washed with water, dissolved in methylene chloride, dried over magnesium sulfate, filtered and evaporated leaving a gum. This gum is subjected to conventional chromatographic separation. The recovered product is dissolved in methylene chloride, filtered through diatomaceous earth, reevaporated and dried in vacuo over phosphorous pentoxide giving the desired product.

EXAMPLE 24

(Glc 1α,4)6 glc 1β,6 gal 1α,6 glc

A 1.0 g. portion of (glc 1α,4)6 glc 1β,6 gal 1α,6 glc nonacosaacetate is dissolved by swirling at room temperature in 16 ml. of a mixture of methanol, water and triethylamine (6:2:3). The solution is allowed to stand for 18 hours and then is concentrated in vacuo at 50° C. The residue is dissolved in 5 ml. of water. A small amount of charcoal is added and the mixture is swirled, filtered through diatomaceous earth, evaporated at 50° C. to a gum and dried in vacuo over phosphorous pentoxide. This material is dissolved in 2 ml. of water and filtered through diatomaceous earth. To the filtrate is added 5 ml. of methanol and then ether. The solvent is decanted from the resulting precipitate and the gum is triturated twice with fresh ether. The solid is then dried at 110° C. in vacuo over phosphorous pentoxide. This solid is dissolved in a small amount of methanol and ether is added giving a gum. The solvents are decanted, fresh ether is added and the solid is collected and dried overnight over phosphorous pentoxide in vacuo giving the desired product.

EXAMPLE 25

(Glc $1\alpha,4)_6$ glc $1\beta,6$ gal $1\alpha,6$ glc nonacosakis (H-sulfate) nonacosasalt with trimethylamine A 100 mg. portion of (glc $1\alpha,4)_6$ glc $1\beta,6$ gal $1\alpha,6$ glc is added to 1 ml. of dimethylformamide. A 327 mg. portion of trimethylamine sulfur trioxide is added and the procedure of Example 5 is followed giving the desired product as a white solid.

EXAMPLE 26

(Glc $1\alpha,4)_6$ glc $1\beta,6$ gal $1\alpha,6$ glc nonacosakis (H-sulfate) nonacosasodium salt A 200 mg. portion of (glc $1\alpha,4)_6$ glc $1\beta,6$ gal $1\alpha,6$ glc nonacosakis (H-sulfate), nonacosasalt with trimethylamine is dissolved in 1–2 ml. of water and then filtered. A 1.0 ml. portion of 30% aqueous sodium acetate solution is added to the filtrate and the procedure of Example 6 is followed, giving the desired product as a white solid.

EXAMPLE 27

| Preparation of Compressed Tablet | |
|---|---|
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 28

| Preparation of Compressed Tablet - Sustained Action | |
|---|---|
| Ingredient | mg/Tablet |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 29

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 30

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 31

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 32

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 33

| Preparation of Injectable Solution | |
|---|---|
| Ingredient | % W/V |
| Active Compound | 0.05–5 |
| Benzyl Alcohol N.F. | 0.9 |
| Water for Injection | 100.0 |

EXAMPLE 34

| Preparation of Injectable Oil | |
|---|---|
| Ingredient | % W/V |
| Active Compound | 0.05–5 |
| Benzyl Alcohol | 1.5 |
| Sesame Oil qs ad | 100.0 |

EXAMPLE 35

Preparation of Intra-Articular Product

| Ingredient | Amount |
|---|---|
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 36

Preparation of Injectable Depo Suspension

| Ingredient | % W/V |
|---|---|
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 37

Preparation of Dental Paste

| Ingredient | % W/W |
|---|---|
| Active Compound | 0.05-5 |
| Zinc Oxide | 15 |
| Polyethylene Glycol 4000 USP | 50 |
| Distilled Water qs | 100 |

EXAMPLE 38

Preparation of Dental Ointment

| Ingredient | % W/W |
|---|---|
| Active Compound | 0.05-5 |
| Petrolatum, White USP qs | 100 |

EXAMPLE 39

Preparation of Dental Cream

| Ingredient | % W/W |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 40

Preparation of Topical Cream

| Ingredient | % W/W |
|---|---|
| Active Compound | 0.05—5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 41

Preparation of Topical Ointment

| Ingredient | % W/W |
|---|---|
| Active Compound | 0.05-5 |
| Cholesterol | 3 |
| Stearyl Alcohol | 3 |
| White Wax | 8 |
| Petrolatum, White USP qs | 100 |

EXAMPLE 42

Preparation of Spray Lotion (non-Aerosol)

| Ingredient | % W/W |
|---|---|
| Active Compound | 0.05—5 |
| Isopropyl Myristate | 20 |
| Alcohol (Denatured) qs | 100 |

EXAMPLE 43

Preparation of Buccal Tablet

| Ingredient | g/Tablet |
|---|---|
| Active Ingredient | 0.00325 |
| 6 × Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 44

Preparation of Lozenge

| Ingredient | g/Lozenge |
|---|---|
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized

We claim:

1. A compound of the formula:

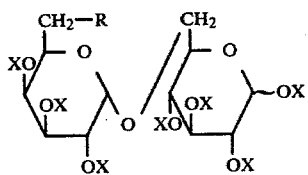

wherein X is SO₃A; wherein A is a pharmaceutically acceptable salt cation; and R is selected from the group consisting of OX,

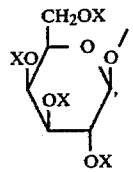

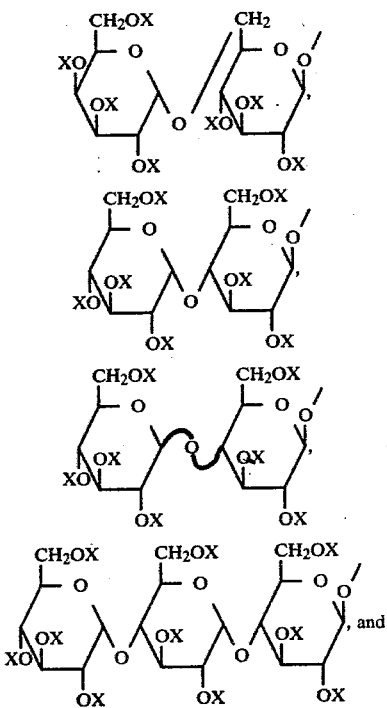
, and

-continued

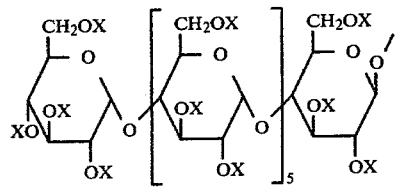

2. The compound according to claim 1, gal 1α,6 glc octakis (H-sulfate), octasalt with trimethylamine.

3. The compound according to claim 1, gal 1α,6 glc octakis (H-sulfate), octasodium salt.

4. The compound according to claim 1, gal 1β,6 gal 1α,6 glc undecakis (H-sulfate), undecasalt with trimethylamine.

5. The compound according to claim 1, gal 1β,6 gal 1α,6 glc undecakis (H-sulfate), undecasodium salt.

6. The compound according to claim 1, gal 1α,6 glc 1β,6 gal 1α,6 glc tetradecakis (H-sulfate), tetradecasalt with trimethylamine.

7. The compound according to claim 1, gal 1α,6 glc 1β,6 gal 1α,6 glc tetradecakis (H-sulfate), tetradecasodium salt.

8. The compound according to claim 1, glc 1α,4 glc 1β,6 gal 1α,6 glc tetradecakis (H-sulfate), tetradecasalt with trimethylamine.

9. The compound according to claim 1, glc 1α,4 glc 1β,6 gal 1α,6 glc tetradecakis (H-sulfate), tetradecasodium salt.

10. The compound according to claim 1, glc 1β,4 glc 1β,6 gal 1α,6 glc tetradecakis (H-sulfate), tetradecasalt with trimethylamine.

11. The compound according to claim 1, glc 1β,4 glc 1β,6 gal 1α,6 glc tetradecakis (H-sulfate), tetradecasodium salt.

12. The compound according to claim 1, (glc 1α,4)₂ glc 1β,6 gal 1α,6 glc heptadecakis (H-sulfate), heptadecasalt with trimethylamine.

13. The compound according to claim 1, (glc 1α,4)₂ glc 1β,6 gal 1α,6 glc heptadecakis (H-sulfate), heptadecasodium salt.

14. The compound according to claim 1, (glc 1α,4)₆ glc 1β,6 gal 1α,6 glc nonacosakis (H-sulfate), nonacosasalt with trimethylamine.

15. The compound according to claim 1, (glc 1α,4)₆ glc 1β,6 gal 1α,6 glc nonacosakis (H-sulfate), nonacosasodium salt.

* * * * *